(12) United States Patent
Ding et al.

(10) Patent No.: US 12,167,909 B2
(45) Date of Patent: Dec. 17, 2024

(54) METHOD AND SYSTEM FOR MAGNETIC RESONANCE IMAGING

(71) Applicant: SHANGHAI UNITED IMAGING HEALTHCARE CO., LTD., Shanghai (CN)

(72) Inventors: Yu Ding, Houston, TX (US); Qi Liu, Houston, TX (US); Jian Xu, Houston, TX (US); Jingyuan Lyu, Houston, TX (US); Yuan Zheng, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 189 days.

(21) Appl. No.: 17/929,679

(22) Filed: Sep. 2, 2022

(65) Prior Publication Data
US 2023/0062908 A1   Mar. 2, 2023

(30) Foreign Application Priority Data

Sep. 2, 2021   (CN) .......................... 202111023626.0

(51) Int. Cl.
*A61B 5/055*   (2006.01)
*A61B 5/00*   (2006.01)
*G01R 33/563*   (2006.01)
*G01R 33/567*   (2006.01)

(52) U.S. Cl.
CPC ............ *A61B 5/055* (2013.01); *A61B 5/7285* (2013.01); *G01R 33/56308* (2013.01); *G01R 33/5673* (2013.01)

(58) Field of Classification Search
CPC ..... A61B 5/0013; A61B 5/0044; A61B 5/055; A61B 5/7285; A61B 5/7289; G01R 33/56308; G01R 33/56325; G01R 33/5673; G16H 30/40; G16H 50/20
See application file for complete search history.

(56) References Cited

U.S. PATENT DOCUMENTS 9,121,915 B2   9/2015  Wu et al.
2020/0333416 A1*  10/2020  Moeller ............. G01R 33/5608

FOREIGN PATENT DOCUMENTS

CN   106419917 B   2/2017

OTHER PUBLICATIONS

Peter Kellman et al., Fully Automatic, Retrospective Enhancement of Real-time Acquired Cardiac Cine MR Images Using Image-based Navigators and Respiratory Motion-corrected Averaging, Magnetic Resonance in Medicine, 59(4):771-778, 2008.

(Continued)

*Primary Examiner* — Michael T Rozanski
(74) *Attorney, Agent, or Firm* — METIS IP LLC

(57) ABSTRACT

The present disclosure may provide imaging methods, systems and storage media. The imaging methods may include: obtaining first imaging data acquired by an imaging device, wherein the first imaging data includes data corresponding to a plurality of cardiac cycles; and performing image reconstruction on data corresponding to the plurality of cardiac cycles in the first imaging data to acquire one or more cardiac cines. Each cardiac cine of the one or more cardiac cines may include cardiac images of a plurality of phases in at least one cardiac cycle.

20 Claims, 6 Drawing Sheets

(56) References Cited

OTHER PUBLICATIONS

Peter Kellman et al., High Spatial and Temporal Resolution Cardiac Cine MRI from Retrospective Reconstruction of Data Acquired in Real Time Using Motion Correction and Resorting, Magnetic Resonance in Medicine, 62(6):1557-1564, 2009.

Xue, Hui et al., High Spatial and Temporal Resolution Retrospective Cine Cardiovascular Magnetic Resonance from Shortened Free Breathing Real-time Acquisitions, Journal of Cardiovascular Magnetic Resonance, 2013, 15 pages.

\* cited by examiner

METHOD AND SYSTEM FOR MAGNETIC RESONANCE IMAGING

CROSS-REFERENCE TO RELATED APPLICATIONS

The application claims priority to Chinese Patent Application No. CN 202111023626.0, filed on Sep. 2, 2021, the contents of which are hereby incorporated by reference to its entirety.

TECHNICAL FIELD

The present disclosure generally relates to imaging field, in particular, to imaging methods, systems and storage media.

BACKGROUND

Cardiac cine imaging may be used to observe a systolic motion of a myocardium and quantitatively calculate various parameters (such as ejection fraction, myocardial mass, etc.) that reflect cardiac functions. Cardiac cine imaging may be an important medical imaging technique to assist diagnosis. If a dynamic image of a high quality needs to be acquired, a relatively large amount of data may need to be acquired. During an acquisition process, a patient may be unable to hold the breath for a long time, and/or the patient may have arrhythmias, which may increase a difficulty of data processing. Therefore, a method for better generating cardiac cines may be needed.

SUMMARY

According to one aspect of the present disclosure, an imaging method may be provided. In some embodiments, the imaging method may be the method for magnetic resonance imaging. The imaging method may include: obtaining first imaging data acquired by an imaging device, wherein the first imaging data includes data corresponding to a plurality of cardiac cycles; performing image reconstruction on data corresponding to the plurality of cardiac cycles in the first imaging data to acquire one or more cardiac cines. Each cardiac cine of the one or more cardiac cines may include cardiac images of a plurality of phases in at least one cardiac cycle.

In some embodiments, the first imaging data may include a first data segment and a second data segment. The first data segment and the second data segment may correspond to a same phase of one or more cardiac cycles. The first data segment may be acquired according to a first distribution. The second data segment may be acquired according to a second distribution. The first distribution and the second distribution may be different. The cardiac cine may include a first cine and a second cine. At least one of the first distribution and the second distribution may satisfy an integrity requirement for reconstructing a first image. The first image may belong to the first cine. The first data segment and the second data segment may be used to reconstruct a second image. The second image may belong to the second cine.

In some embodiments, an acquisition rate of a union of the first distribution and the second distribution in a central region of k-space may be higher than an acquisition rate in an edge region.

In some embodiments, the method may further include: acquiring reference information; and determining the plurality of phases from the first imaging data based on the reference information.

In some embodiments, the reference information may be acquired based on at least one cardiac cine of the one or more cardiac cines.

In some embodiments, the method may further include: acquiring the first imaging data by performing abnormal processing on second imaging data acquired from the imaging device.

In some embodiments, the abnormal processing may include removing abnormal data. The abnormal data may include data corresponding to abnormal heart rhythms or abnormal breathing.

In some embodiments, the one or more cardiac cines may include a first cine and a second cine, and the performing image reconstruction on data corresponding to the plurality of cardiac cycles in the first imaging data to acquire one or more cardiac cines may include: performing image reconstruction on the first imaging data to obtain the first cine; performing conversion processing based on the first cine to acquire third imaging data, the third imaging data including k-space data, the conversion processing including an inverse reconstruction of k-space data based on a third image, the third image being acquired at a selected time point; combining a plurality of parts of the third imaging data corresponding to a same phase in the plurality of cardiac cycles according to the reference information to acquire fourth imaging data, the reference information being configured to locate phases of the plurality of cardiac cycles; and performing image reconstruction on the fourth imaging data to obtain the second cine.

In some embodiments, the conversion processing may further include: extracting a respiratory motion signal from the first cine before the inverse reconstruction; performing respiratory motion compensation on at least a part of the third image according to a cardiac motion signal and the respiratory motion signal.

In some embodiments, the method may further include: determining output dynamic cine information based on one or more quality evaluation results of the one or more cardiac cines.

In some embodiments, the method may further include: acquiring at least one of a cardiac motion signal or a respiratory motion signal for quality evaluation.

According to another aspect of the present disclosure, an imaging system may be provided. In some embodiments, the imaging system may be the system for magnetic resonance imaging. The system may include: a data acquisition module, configured to obtain first imaging data acquired by an imaging device, wherein the first imaging data includes data corresponding to a plurality of cardiac cycles; and a reconstruction module, configured to perform image reconstruction based on data corresponding to the plurality of cardiac cycles in the first imaging data to acquire one or more cardiac cines; wherein each cardiac cine of the one or more cardiac cines includes cardiac images of a plurality of phases in at least one cardiac cycle.

In some embodiments, the first imaging data may include a first data segment and a second data segment. The first data segment and the second data segment may correspond to a same phase of one or more cardiac cycles. The first data segment may be acquired according to a first distribution. The second data segment may be acquired according to a second distribution. The first distribution and the second distribution may be different. The cardiac cine may include a first cine and a second cine. At least one of the first distribution and the second distribution may satisfy an integrity requirement for reconstructing a first image. The first image may belong to the first cine. The first data segment and the second data segment may be used to reconstruct a second image. The second image may belong to the second cine.

In some embodiments, an acquisition rate of a union of the first distribution and the second distribution in a central region of k-space may be higher than an acquisition rate in an edge region.

In some embodiments, the system may further include: acquiring reference information; and determining the plurality of phases from the first imaging data based on the reference information.

In some embodiments, the one or more cardiac cines may include a first cine and a second cine, and the performing image reconstruction on data corresponding to the plurality of cardiac cycles in the first imaging data to acquire one or more cardiac cines may include: performing image reconstruction on the first imaging data to obtain the first cine; performing conversion processing based on the first cine to acquire third imaging data, the third imaging data including k-space data, the conversion processing including an inverse reconstruction of k-space data based on a third image, the third image being acquired at a selected time point; combining a plurality of parts of the third imaging data corresponding to a same phase in the plurality of cardiac cycles according to the reference information to acquire fourth imaging data, the reference information being configured to locate phases of the plurality of cardiac cycles; and performing image reconstruction on the fourth imaging data to obtain the second cine.

In some embodiments, the conversion processing may further include: extracting a respiratory motion signal from the first cine before the inverse reconstruction; performing respiratory motion compensation on at least a part of the third image according to a cardiac motion signal and the respiratory motion signal.

In some embodiments, the system may further include: determining output dynamic cine information based on one or more quality evaluation results of the one or more cardiac cines.

In some embodiments, the system may further include: acquiring at least one of a cardiac motion signal or a respiratory motion signal for quality evaluation.

According to an aspect of the present disclosure, a non-transitory computer readable medium may be provided. The non-transitory computer readable medium may include at least one set of instructions, wherein when executed by at least one processor of a computing device, the at least one set of instructions may cause the at least one processor to effectuate a system comprising: obtaining first imaging data acquired by a magnetic resonance device, wherein the first imaging data includes data corresponding to a plurality of cardiac cycles; performing image reconstruction on data corresponding to the plurality of cardiac cycles in the first imaging data to acquire one or more cardiac cines; wherein each cardiac cine of the one or more cardiac cines includes cardiac images of a plurality of phases in at least one cardiac cycle.

According to another aspect of the present disclosure, a method for magnetic resonance imaging (MRI) may be provided. The method may include: acquiring first imaging data acquired by an MR device in a real-time dynamic cine imaging manner, the first imaging data including data corresponding to at least two cardiac motion cycles; performing image reconstruction based on the first imaging data to acquire a real-time dynamic cine and an electrocardiographic (ECG) gated cardiac cine; and outputting the real-time dynamic cine and the ECG gated cardiac cine. At least one of the real-time dynamic cine or the ECG gated cardiac cine may include cardiac images of a plurality of phases in at least one cardiac motion cycle.

In some embodiments, the performing image reconstruction based on the first imaging data to acquire a real-time dynamic cine and an electrocardiographic (ECG) gated cardiac cine may include: performing the image reconstruction based on the first imaging data to acquire the real-time dynamic cine; combining a part of the first imaging data corresponding to a same phase in each cardiac motion cycle according to reference information to acquire second imaging data, wherein the reference information is used to locate one or more phases of the at least two cardiac motion cycles; and performing the image reconstruction based on the second imaging data to acquire the ECG gated cardiac cine.

In some embodiments, before performing image reconstruction based on the first imaging data to acquire an ECG gated cardiac cine, the method may further include: removing a first part of the first imaging data corresponding to non-target respiratory states from the first imaging data to retain a second part of the first imaging data corresponding to a target respiratory state. The performing image reconstruction based on the first imaging data to acquire a real-time dynamic cine and an ECG gated cardiac cine may include: performing the image reconstruction based on the first imaging data to acquire the real-time dynamic cine; combining a part of the second part of the first imaging data corresponding to a same phase in each cardiac motion cycle according to reference information to acquire second imaging data, wherein the reference information is used to locate one or more phases of the at least two cardiac motion cycles; and performing the image reconstruction based on the second imaging data to acquire the ECG gated cardiac cine.

In some embodiments, the performing image reconstruction based on the first imaging data to acquire a real-time dynamic cine and an ECG gated cardiac cine may include: performing the image reconstruction based on the first imaging data to acquire the real-time dynamic cine; restoring the real-time dynamic cine to a k-space to acquire third imaging data; combining a part of the third imaging data corresponding to a same phase in each cardiac motion cycle according to reference information to acquire fourth imaging data, wherein the reference information is used to locate one or more phases of the at least two cardiac motion cycles; and performing the image reconstruction based on the fourth imaging data to acquire the ECG gated cardiac cine.

In some embodiments, the reference information may include a cardiac motion signal. The method may further include: extracting the cardiac motion signal from the real-time dynamic cine.

In some embodiments, the reference information may include a cardiac motion signal. The method may further include: extracting a cardiac motion signal and a respiratory motion signal from the real-time dynamic cine; performing respiratory motion compensation on the real-time dynamic cine according to the cardiac motion signal and the respiratory motion signal to acquire a compensated real-time dynamic cine. The restoring the real-time dynamic cine to a k-space may include: restoring the compensated real-time dynamic cine to the k-space.

In some embodiments, the reference information may include or be derived from at least one of ECG, a pulse signal, or a cardiac motion signal.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting schematic embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "device," "unit," "module," and/or "block" used herein are one method to distinguish different components, elements, parts, sections or assembly of different levels in ascending order. However, the terms may be displaced by another expression if they achieve the same purpose.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including" when used in this disclosure, specify the presence of stated features, integers, steps, operations, elements, and/or components, but do not preclude the presence or addition of one or more other features, integers, steps, operations, elements, components, and/or groups thereof.

The flowcharts used in the present disclosure illustrate operations that systems implement according to some embodiments in the present disclosure. It is to be expressly understood, the operations of the flowchart may be implemented not in order. Conversely, the operations may be implemented in an inverted order, or simultaneously. Moreover, one or more other operations may be added to the flowcharts. One or more operations may be removed from the flowcharts.

Figure 1:
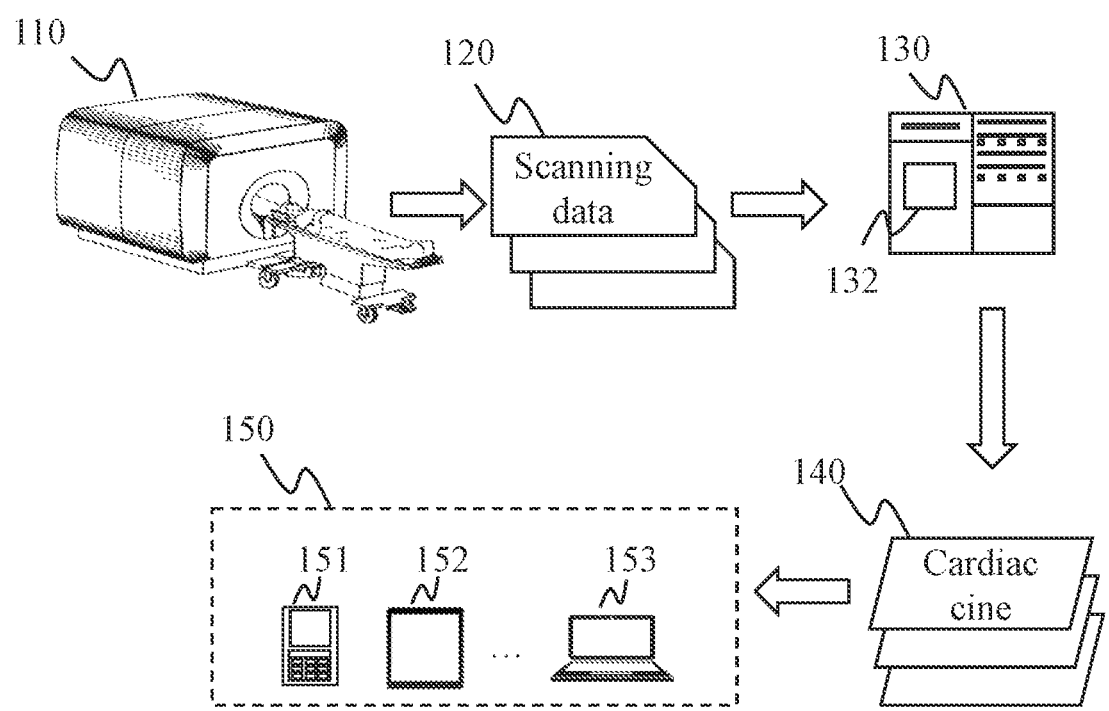
FIG. 1 is a schematic diagram of an application scenario of an imaging system according to some embodiments of the present disclosure.

FIG. 1 is a schematic diagram of an application scenario of an imaging system according to some embodiments of the present disclosure.

As shown in FIG. 1, an application scenario may include an imaging device 110, a processing device 130, a terminal device 150, scanning data 120, and a cardiac cine 140. The imaging device 110 may scan an object to acquire the scanning data 120. The processing device 130 may process the scanning data 120 to generate the cardiac cine 140. The cardiac cine 140 may be displayed on the terminal device 150. The application scenario may also include a network, a storage device, etc. The processing device 130 may include a processor 132.

The imaging device 110 may refer to a device that scans the object through information acquisition to acquire internal information of the object. As used herein, the object may include but be not limited to a human body, an organ, a damaged part, a tumor, a phantom, etc. In some embodiments, the imaging device 110 may include a magnetic resonance imaging (MRI) device.

Nuclear magnetic resonance imaging (NMRI), also referred to as spin imaging or magnetic resonance imaging (MRI), may utilize a principle of nuclear magnetic resonance. According to different attenuation of released energy in different structural environments within the object, a position, and type of the atomic nucleus of the object may be determined by detecting an electromagnetic wave emitted by an applied gradient magnetic field, such that an anatomical image inside the object may be determined accordingly. MRI technology may acquire a clear image of a high contrast inside the sample/tissue without damage and ionizing radiation. MRI technology has been widely used in various fields, especially in medical diagnosis.

An MRI device may include a magnet module and a radio frequency (RF) module (not shown in FIG. 1). In some embodiments, the MR scanning device may perform a scan on the object, such as a patient, or a region of an object. In some embodiments, the scan may be a locating scan for locating the object or the region of the object, and/or identifying the object or the region of the object. In some embodiments, the scan may be a pre scan (or pre-scan) for calibrating the imaging scan. In some embodiments, the scan may be an imaging scan for generating an image.

The magnet module may include a main magnetic field generator and/or a gradient magnetic field generator (not shown in FIG. 1). The main magnetic field generator may create a static magnetic field BO during the scan. The main magnet may be of various types, for example, a permanent magnet, a super conductive magnet, a resistive electromagnet, or the like.

The gradient magnetic field generator may generate a gradient magnetic field in a certain direction (e.g., X, Y, or Z direction) in the main magnetic field BO. As used herein, the X, Y, and Z directions may represent X, Y, and Z axes in a coordinate system. Merely by way of example, the X and Z axes may be in a horizontal plane, the X and Y axes may be in a vertical plane, and the Z axis may be along a rotation axis of a gantry. In some embodiments, the X-axis, Y-axis, and Z-axis may be designated by the gradient magnetic field generator (i.e., a gradient coil in the gradient magnetic field generator). The gradient magnetic field may encode and/or read spatial information of the object (or the region of the object) located within the MR scanning device.

In some embodiments, the magnet module may generate a gradient magnetic field in a plurality of directions during the scan. Merely by way of example, the magnet module may generate a first gradient magnetic field in a first direction, a second gradient magnetic field in a second direction, and a third gradient magnetic field in a third direction. In some embodiments, the first, second, and third directions may be along the X-axis, the Y-axis, and the Z-axis, respectively. In some embodiments, the gradient magnetic field along the X-axis, Y-axis, and/or Z-axis may correspond to different encoding/readout directions in a k-space (e.g., kx-axis direction, ky-axis direction, kz-axis direction, or other directions).

A function, size, type, shape, position, amount, and/or amplitude of the magnet module and/or the RF module may be determined or varied according to one or more specific conditions. Merely by way of example, the magnet module and the radio frequency (RF) module may be designed to surround the object (or the region of the object) to form a tunnel type MR scanning device (i.e., a closed-bore MR scanning device) or an open type MR scanning device (i.e., an open-bore MR scanning device). In some embodiments, RF coils may include a transmitting coil and a receiving coil. These RF coils may transmit or receive RF signals to/from the object (or the region of the object). Merely by way of example, the transmitting coil may transmit RF energy to the object (or the region of the object) to induce an electrical signal in a region of interest (ROI). As another example, the receiving coil may pick up RF electromagnetic radiation generated by nuclear relaxation inside the object (or the region of the object).

In some embodiments, the RF coils may include volume coils and local coils according to different functions and/or sizes. In some embodiments, the volume coil(s) may include a body coil, a birdcage coil, a transverse electromagnetic coil, a saddle coil, or the like. In some embodiments, the local coil(s) may include a solenoid coil, a saddle coil, a flexible coil, a surface coil, or the like.

The surface coil may be a coil placed directly on the object (or the region of the object). In some embodiments, the surface coil may be a receiving coil configured to receive a signal generated by nuclear relaxation inside the object (or the region of the object). Merely by way of example, the surface coil may receive a plurality of MR signals during a pre scan (or pre-scan) and/or an imaging scan. For example, the surface coil may be placed directly on the ROI of the object, thereby providing an improved signal-to-noise ratio (SNR) by limiting a spatial range of reception. In some embodiments, the surface coil may be a ring made of a conductive material. Merely by way of example, the surface coil may be a copper tube. In some embodiments, the ring may be formed in various shapes. Merely by way of example, the ring may be bent to conform to a body portion to be examined. In some embodiments, the RF module may include one or more surface coils.

The body coil may be a coil surrounding the object (or the region of the object). Merely by way of example, the body coil may surround the head or knee of a patient being examined. In some embodiments, the body coil may be a receiving coil configured to receive a signal generated by nuclear relaxation inside the object (or the region of the object), and/or a transmitting coil configured to transmit RF energy to the object (or the region of the object). Merely by way of example, the body coil may receive a plurality of MR signals during a pre scan (or pre-scan) and/or an imaging scan.

In some embodiments, the RF module may include one or more receiving coils. The receiving coil(s) may include a surface coil and/or a body coil. Merely by way of example, the RF module may include a first receiving coil and a second receiving coil. Both the first receiving coil and the second receiving coil may be surface coils. As another example, both the first receiving coil and the second receiving coil may be body coils. In some embodiments, the RF module may include one or more individual coils.

In some embodiments, the imaging device 110 may include other devices, for example, a computed tomography (CT) device.

The scanning data 120 may be data acquired by the imaging device 110 for scanning the object, e.g., first imaging data. For example, the scanning data 120 may be k-space data acquired by the imaging device 110. Merely by way of example, MR signals may be filled into the k-space to generate a k-space data set, and the k-space data set may include part of data in the k-space (such as data in a central region of the k-space) or all of the data. As used herein, MRI data acquired by the MR device may be the k-space data. In MRI physics, the k-space may be a 2D or 3D Fourier transform of an MR image domain. Data acquired from the MR signals (e.g., echoes or echo signals) may be referred to as the k-space data. Sampled k-space data may include spatial data of each imaging slice of the object, and thus may be arranged in an array, e.g., the k-space. Each k-space data entry (or a k-space data point) may provide frequency and phase information. The $k_x$ axis and the $k_y$ axis of the k-space may correspond to a horizontal axis (the X axis) and a vertical axis (the Y axis) of an image (e.g., a desired slice of a target). An MR image may be generated from the k-space data arranged in the k-space by applying an inverse Fourier transform, etc. A center of the k-space may correspond to low spatial frequency information to determine a contrast and brightness of an overall image. A periphery of the k-space may correspond to high spatial frequency information to determine edges, details and sharpening transitions of the image. Each k-space data point may be a complex number including a real number and an imaginary number, or each k-space data point may be defined as having amplitude and phase information and processed by a triangular relationship. As another example, the scanning data 120 may be projection data acquired by a CT imaging device.

The processing device 130 may process data and/or information acquired from the imaging device 110 and/or the terminal device 150. In some embodiments, the processing device 130 may include a computer, a user console, a single server, a group server, etc. In some embodiments, the processing device 130 may be local or remote. For example, the processing device 130 may access information and/or data stored in the imaging device 110 and/or the terminal device 150 through a network. In some embodiments, the processing device 130 may be directly connected with the imaging device 110 and/or the terminal device 150 to access the information and/or data stored therein. In some embodiments, the processing device 130 may receive information from the imaging device 110 or send information to the imaging device 110, or the like. According to some embodiments, the processing device 130 may receive an instruction from, for example, a user, and adjust the magnet module and/or the RF module to acquire an image of the object (or the region of the object) according to the received instruction. In some embodiments, the processing device 130 may process the MR signals received from the RF module (e.g., surface coils and/or body coils) and generate one or more MR data sets (the MR data sets including a plurality of groups of MR data sampled from the MR signals) or imaging data (e.g., k-space data sets) based on the MR signals. In some embodiments, the processing device 130 may be implemented on a cloud platform. For example, the cloud platform may include a private cloud, a public cloud, a hybrid cloud, or the like, or any combination thereof.

In some embodiments, the processing device 130 may include the processor 132. The processor 132 may process and perform one or more functions described in the present disclosure. For example, the processor 132 may perform weighting processing on at least a portion of scanning data, imaging data (e.g., the scanning data of a low-frequency portion or the k-space center region) to determine data required for reconstructing an image. As another example, the processor 132 may perform data preprocessing, image reconstruction, post-processing, etc., on the scanning data and the imaging data. In some embodiments, the processor 132 may also control scanning actions of the imaging device 110. For example, the processor 132 may control the magnet module and/or the RF module of the imaging device 110. Merely by way of example, the processor 132 may control gradient magnetic fields in the X direction, the Y direction, and the Z direction. In some embodiments, the processor 132 may include one or more sub processors (e.g., a single core processing device, a multi-core processing device). Merely by way of example, the processor 132 may include a central processing unit (CPU), an application specific integrated circuit (ASIC), an application specific instruction processor (ASIP), a graphics processor (GPU), a physical processor (PPU), a digital signal processor (DSP), a field programmable gate array (FPGA), a programmable logic circuit (PLD), a controller, a microcontroller unit, a reduced instruction set computer (RISC), a microprocessor, or the like, or any combination thereof.

The cardiac cine 140 may be a sequence composed of a plurality of image frames and may dynamically reflect a motion of the heart. For example, the cardiac cine may be an MR cardiac cine. The MR cardiac cine may be used to observe a systolic motion of the myocardium and quantitatively determine various parameters (such as ejection fraction, myocardial mass, etc.) that reflect cardiac functions, which is an important medical imaging technology to assist diagnosis. MRI data for image reconstruction may be acquired by scanning a patient, and then a cardiac cine may be acquired by the image reconstruction. It may be understood that the cardiac cine may include cardiac images of a plurality of phases in at least one cardiac motion cycle (also referred to as cardiac cycle). The MR cardiac cine may include two imaging modes: an electrocardiographic (ECG) gated cardiac cine imaging and real-time dynamic cine imaging.

A cardiac cycle may be a process that the heart that completes a physiological motion. For example, the physiological motion of the heart may include one diastolic motion and one systolic motion. The cardiac cycle may be a process of completing the systolic motion and the diastolic motion. As used herein, each cardiac cycle may include a plurality of phases, and each phase may correspond to a static cardiac image. The cardiac image of each phase may reflect the state of the heart in the phase.

The cardiac image may be an image corresponding to scanning data of the heart. In some embodiments, the cardiac image may be acquired by image reconstruction based on the scanning data. The image reconstruction may be performed in various ways.

In some embodiments, a format of the cardiac image may include but be not limited to a joint photographic experts group (JPEG) format, a tagged image file format (TIFF) format, or the like. In some embodiments, the cardiac image may include a two-dimensional (2D) image, a three-dimensional (3D) image, or the like.

The terminal device 150 may display an image (e.g., a cardiac image, a cardiac cine) to a user. In some embodiments, the terminal device 150 may include a mobile device 151, a tablet computer 152, a notebook computer 153, or the like, or any combination thereof.

Any suitable network capable of facilitating exchange of information and/or data of the imaging system 100 may be included. For example, the network may be a part of a hospital network system (HIS), a picture archiving and communication system (PACS), other hospital networks, or networks that are independent from and connected to the HIS, PACS, or the other hospital networks. In some embodiments, one or more components of the imaging system 100 (e.g., the imaging device 110, the terminal device 150, the processing device 130, etc.) may exchange information and/or data with one or more components of the imaging system 100 through the network. For example, the processing device 130 may acquire planning data from a data processing planning system through a network. The network may include a public network (such as Internet), a private network (such as a local area network (LAN), a wide area network (WAN)), a wired network (such as Ethernet), a wireless network (such as a Wi-Fi network), a cellular network (such as a long-term evolution (LTE) network), a frame relay network, a virtual private network (VPN), a satellite network, a telephone network, a router, a hub server computer, or the like, or any combination thereof. For example, the network may include a wired network, an optical fiber network, a telecommunications network, a local area network, a wireless local area network (WLAN), a metropolitan area network (MAN), a public switched telephone network (PSTN), a Bluetooth network, ZigBee™, a near field communication (NFC) network, or the like, or any combination thereof. In some embodiments, the network may include one or more network access points. For example, the network may include wired and/or wireless network access points, such as base stations and/or Internet switching points, through which one or more components of the imaging system 100 may connect to the network to exchange data and/or information.

A storage device may store data (e.g., scanning data, imaging data, etc., of an object), instructions, and/or any other information. In some embodiments, the storage device may store data obtained from the imaging device 110, the terminal device 150, and/or the processing device 130. For example, the storage device may store scanning data and imaging data of an object obtained from the imaging device 110. In some embodiments, the storage device may store data and/or instructions executed or used by the processing device 130 to perform the exemplary methods described in the present disclosure. For example, the storage device may store scanning data of a target scanning region and data acquired by weighing the imaging data. As another example, the storage device may also store real-time perspective image data and/or image data obtained during and/or after reconstruction. In some embodiments, the storage device may include a mass storage, a removable memory, a volatile read-write memory, a read-only memory (ROM), or the like, or any combination thereof. The mass storage may include a magnetic disk, an optical disk, a solid-state disk, a mobile storage, etc. The removable memory may include a flash drive, a floppy disk, an optical disk, a memory card, a Zip disk, a magnetic tape, or the like. The volatile read-write memory may include a random access memory (RAM). The RAM may include a dynamic random access memory (DRAM), a dual data rate synchronous dynamic random access memory (DDR-SDRAM), a static random access memory (SRAM), a silicon controlled random access memory (T-RAM), a zero capacitance random access memory (Z-RAM), or the like. The ROM may include a mask read only memory (MROM), a programmable read only memory (PROM), an erasable programmable read only memory (EPROM), an electrically erasable programmable read only memory (EEPROM), an optical disk read only memory (CD-ROM), a digital multi-function optical disk, or the like. In some embodiments, the storage device may be implemented by a cloud platform described in the present disclosure. For example, the cloud platform may include a private cloud, a public cloud, a hybrid cloud, a community cloud, a distributed cloud, a cross cloud, a multi cloud, or the like, or any combination thereof.

In some embodiments, the storage device may be connected to the network to enable communications with one or more components (e.g., the processing device 130, the terminal device 150, etc.) in the imaging system 100. One or more components in the imaging system 100 may read data or instructions in the storage device through the network. In some embodiments, the storage device may be a part of the processing device 130, or may be independent and directly or indirectly connected to the processing device 130.

Figure 2:
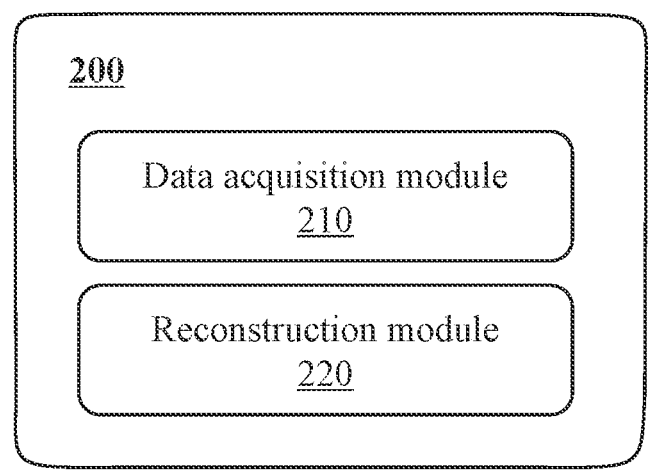
FIG. 2 is a block diagram of an imaging system according to some embodiments of the present disclosure.

FIG. 2 is a block diagram of an imaging system according to some embodiments of the present disclosure. As shown in FIG. 2, the imaging system 200 may include a data acquisition module 210 and a reconstruction module 220.

In some embodiments, the data acquisition module 210 may be configured to obtain first imaging data acquired by an imaging device, wherein the first imaging data includes data corresponding to a plurality of cardiac cycles. In some embodiments, the first imaging data may include a first data segment and a second data segment. The first data segment and the second data segment may correspond to a same phase of one or more cardiac cycles. The first data segment may be acquired according to a first distribution. The second data segment may be acquired according to a second distribution. The first distribution and the second distribution may be different. The cardiac cine may include a first cine and a second cine. At least one of the first distribution and the second distribution may satisfy an integrity requirement for reconstructing a first image. The first image may belong to the first cine. The first data segment and the second data segment may be used to reconstruct a second image. The second image may belong to the second cine. In some embodiments, an acquisition rate of a union of the first distribution and the second distribution in a central region of k-space may be higher than an acquisition rate in an edge region. In some embodiments, the data acquisition module 210 may be further configured to acquire reference information; and determine the plurality of phases from the first imaging data based on the reference information. In some embodiments, the reference information may be acquired based on at least one cardiac cine of the one or more cardiac cines. In some embodiments, the data acquisition module 210 may be further configured to acquire the first imaging data by performing abnormal processing on second imaging data acquired from the imaging device. In some embodiments, the abnormal processing may include removing abnormal data. The abnormal data may include data corresponding to abnormal heart rhythms or abnormal breathing.

In some embodiments, the reconstruction module 220 may be configured to perform image reconstruction on data corresponding to the plurality of cardiac cycles in the first imaging data to acquire one or more cardiac cines. In some embodiments, each cardiac cine of the one or more cardiac cines may include cardiac images of a plurality of phases in at least one cardiac cycle. In some embodiments, the one or more cardiac cines may include a first cine and a second cine. In some embodiments, the reconstruction module 220 may be configured to perform image reconstruction on the first imaging data to obtain the first cine; perform conversion processing based on the first cine to acquire third imaging data, the third imaging data including k-space data, the conversion processing including an inverse reconstruction of k-space data based on a third image, the third image being acquired at a selected time point; combine a plurality of parts of the third imaging data corresponding to a same phase in the plurality of cardiac cycles according to the reference information to acquire fourth imaging data, the reference information being configured to locate (or obtain) phases of the plurality of cardiac cycles; and perform image reconstruction on the fourth imaging data to obtain the second cine. In some embodiments, the conversion processing may further include: extracting a respiratory motion signal from the first cine before the inverse reconstruction; performing respiratory motion compensation on at least a part of the third image according to a cardiac motion signal and the respiratory motion signal. In some embodiments, the reconstruction module 220 may be further configured to determine output dynamic cine information based on one or more quality evaluation results of the one or more cardiac cines. In some embodiments, the reconstruction module 220 may be further configured to acquire at least one of a cardiac motion signal or a respiratory motion signal for quality evaluation.

Figure 3:
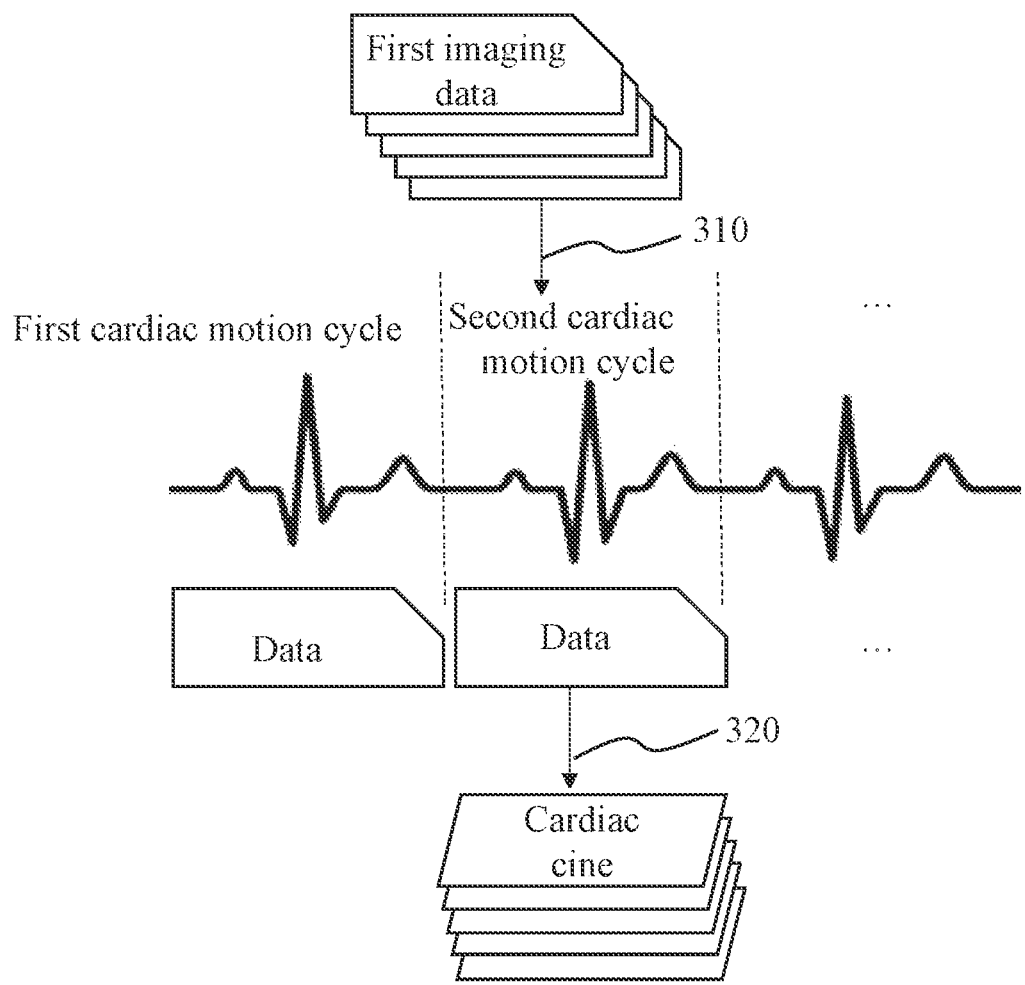
FIG. 3 is a flowchart of an imaging process according to some embodiments of the present disclosure.

FIG. 3 is a flowchart of an imaging process according to some embodiments of the present disclosure. In some embodiments, the process 300 may be performed by the processing device 130 or the imaging system 200.

In 310, first imaging data acquired by an imaging device may be acquired. Specifically, operation 310 may be performed by the data acquisition module 210.

The first imaging data may refer to scanning data acquired by an imaging device, e.g., k-space data acquired by the imaging device. The first imaging data may include scanning data corresponding to a plurality of cardiac cycles. More descriptions of the first imaging data may be found elsewhere in the present disclosure, e.g., FIG. 4 and/or the descriptions thereof.

In 320, image reconstruction may be performed on data corresponding to the plurality of cardiac cycles in the first imaging data to acquire one or more cardiac cines. Each cardiac cine of the one or more cardiac cines may include cardiac images of a plurality of phases in at least one cardiac cycle. Specifically, operation 320 may be performed by the reconstruction module 220.

The image reconstruction may be a process of obtaining an image based on scanning data. For example, the scanning data may be k-space data. A reconstructed image may be an image of a dot matrix format or a dynamic image composed of a plurality of static images.

The image reconstruction may be performed based on a reconstruction algorithm, e.g., an iterative algorithm, an inverse Fourier transform, etc. A reconstruction algorithm based on the inverse Fourier transform may include but be not limited to a SENSE (Sensitivity Encoding) algorithm, a GRAPPA (GeneRalized Autocalibrating Partially Parallel Acquisitions) algorithm, a compressed sensing algorithm based on the SENSE algorithm, or the like, or any combination thereof. One or more parameters in the reconstruction algorithm may be acquired from one or more reference images. As used herein, the k-space data of the reference image may be fully sampled, or the k-space center of the reference image may be fully sampled. In some embodiments, the reference image may be sampled separately. In some embodiments, the scanning data may be combined to acquire the reference image, for example, all scanning data may be averaged in a time dimension to acquire the reference image. Of course, the present disclosure does not make any restriction on the specific acquisition manner of the reference image.

In some embodiments, the cardiac cine may include cardiac images of a plurality of phases within at least one cardiac cycle. A phase may refer to a time difference between a time point and a starting point of a cardiac cycle in the cardiac cycle. Of course, other reference points in the cardiac cycle may also be used instead of the starting point of the cardiac cycle. In some embodiments, the phase may be a time point in the cardiac cycle. For example, assuming that the cardiac cycle is 800 ms, the first phase may be a time point in the cardiac cycle that is 20 ms with respect to the starting point of the cardiac cycle. In some embodiments, the phase may be a time period in the cardiac cycle.

Since a cardiac cine is composed of cardiac images including a plurality of phases, the cardiac cine may reflect the cardiac motion (also referred to as heart motion) better.

In some embodiments, the reconstruction module 220 may perform the image reconstruction on the scanning data corresponding to the first imaging data in a plurality of time periods, acquire a cardiac image frame corresponding to each time period, and acquire the cardiac cine based on cardiac images corresponding to the plurality of time periods. As used herein, the plurality of time periods may include time periods corresponding to different phases.

It may be understood that the first imaging data acquired by the MR device may be the k-space data. In some embodiments, the first imaging data may need to be reconstructed to acquire a second cine (e.g., an ECG gated cardiac cine). The imaging of a first cine (e.g., real-time dynamic cine imaging) may acquire k-space data at a relatively high acceleration ratio and a fixed time interval. The k-space data acquired in one cardiac cycle may be not enough to complete the reconstruction of the cardiac image, so it may be necessary to acquire data (i.e., the k-space data) corresponding to at least two cardiac cycles. Referring to the above introduction of the ECG gated cardiac cine reconstruction, positions of data corresponding to a same phase of different cardiac cycles in the first imaging data in the k-space may be as different as possible (i.e., try to avoid acquiring the k-space data at repeated positions) to ensure a quality/effect of a reconstructed cardiac image. It may be worth noting that due to a periodicity of the heart motion, for images in a same phase, it is easy to acquire highly redundant data in the k-space of the image at repeated positions in different periods. Such data acquisition manner may be considered to be inefficient.

Data corresponding to each phase may correspond to a certain count of k-space data lines. In some embodiments, imaging data (e.g., a plurality of k-space data sets) may be divided into a plurality of phases based on the certain count of k-space data lines. For example, the imaging data corresponding to two k-space data lines acquired continuously may be taken as data corresponding to one phase. In some embodiments, a time interval of the acquisition of the first imaging data may be determined based on the phase. For example, assuming that a cardiac cycle is 800 ms, and is divided into 20 phases, that is, one phase is 40 ms, then k-space data corresponding to a plurality of phases may be acquired continuously at a time interval of 40 ms to acquire the first imaging data.

In some embodiments, one image frame in the cardiac cine may be acquired by fusing a plurality of image frames, and the plurality of image frames may belong to different cardiac cycles and correspond to a same phase.

In some embodiments, the processing device 130 may acquire reference information, and determine the plurality of phases from the first imaging data based on the reference information.

The reference information may reflect a physiological motion. In some embodiments, the reference information may include a cardiac motion signal, a respiratory motion signal, a pulse signal, or the like, or any combination thereof. The reference information may be acquired in various ways. For example, the cardiac motion signal may be acquired by electrocardiogram (ECG) (also referred to as electro-cardio signal).

In some embodiments, the reference information may be acquired based on at least one cardiac cine. It is worth mentioning that a technology for extracting signals from cardiac cines and performing data processing based on the extracted signals may be collectively referred to as self-gating (SG) technology. For example, an extraction of the cardiac motion signal and/or the respiratory motion signal from the real-time dynamic cine and respiratory motion compensation according to the cardiac motion signal and/or the respiratory motion signal mentioned in the present disclosure may be realized by the self-gating technology.

In some embodiments, the cardiac motion signal may be acquired by a technique such as an image recognition.

In some embodiments, a corresponding relationship between the cardiac motion and time may be acquired based on the reference information. The plurality of phases in the first imaging data may be determined based on a corresponding relationship between the first imaging data and time, that is, a time relationship between data and the starting point of the cardiac motion cycle may be determined.

In some embodiments, the first imaging data may be acquired by performing abnormal processing based on second imaging data acquired from an MR device.

The second imaging data may be original scanning data acquired by the imaging device or scanning data after some processing. For example, the second imaging data may include raw k-space data.

The abnormal processing may include various manners, such as noise reduction processing. In some embodiments, the abnormal processing may include removing abnormal data. The abnormal data may include data corresponding to abnormal heart rhythms and/or the abnormal breathing.

In some embodiments, corresponding abnormal data in the second imaging data may be determined based on the reference information. For example, based on a time corresponding to an abnormal waveform in the ECG, data corresponding to the time in the second imaging data may be determined as data corresponding to the abnormal heart rhythms. As another example, based on a time corresponding to an abnormal breathing frequency in a respiratory motion signal, data corresponding to the time in the second imaging data may be determined as data corresponding to the abnormal breathing.

In some embodiments, image reconstruction may be performed based on the second imaging data to acquire a first image. The corresponding abnormal data in the second imaging data may be determined based on the first image. In some embodiments, one or more feature points in the first image may be used to evaluate whether a respiratory motion exists. For example, a position of a diaphragm in an image may be recognized. The one or more feature points may be determined based on the position of the diaphragm. Whether the abnormal breathing exists may be determined by tracking a motion (i.e., a motion of the diaphragm) of the one or more feature points in a cardiac cine.

In some embodiments, the data acquisition module 210 may acquire the first imaging data by removing scanning data of time points/phases/cardiac cycles corresponding to the abnormal heart rhythms and/or the abnormal breathing from the second imaging data.

For example, the data acquisition module 210 may remove a first portion of the imaging data (i.e., scanning data of time points/phases/cardiac cycles corresponding to abnormal breathing) corresponding to non-target respiratory states from the first imaging data to retain a second portion of the imaging data corresponding to a target respiratory state. The respiratory motion may be continuously circulated in three stages (i.e., in respiratory states), namely, an inhalation, an exhalation, and breath holding. In a breath-holding stage, the heart may be considered to be always kept at one position, so the second portion of the imaging data corresponding to the breath holding stage state (i.e., the target respiratory state) may be reserved for the image reconstruction.

Figure 4:
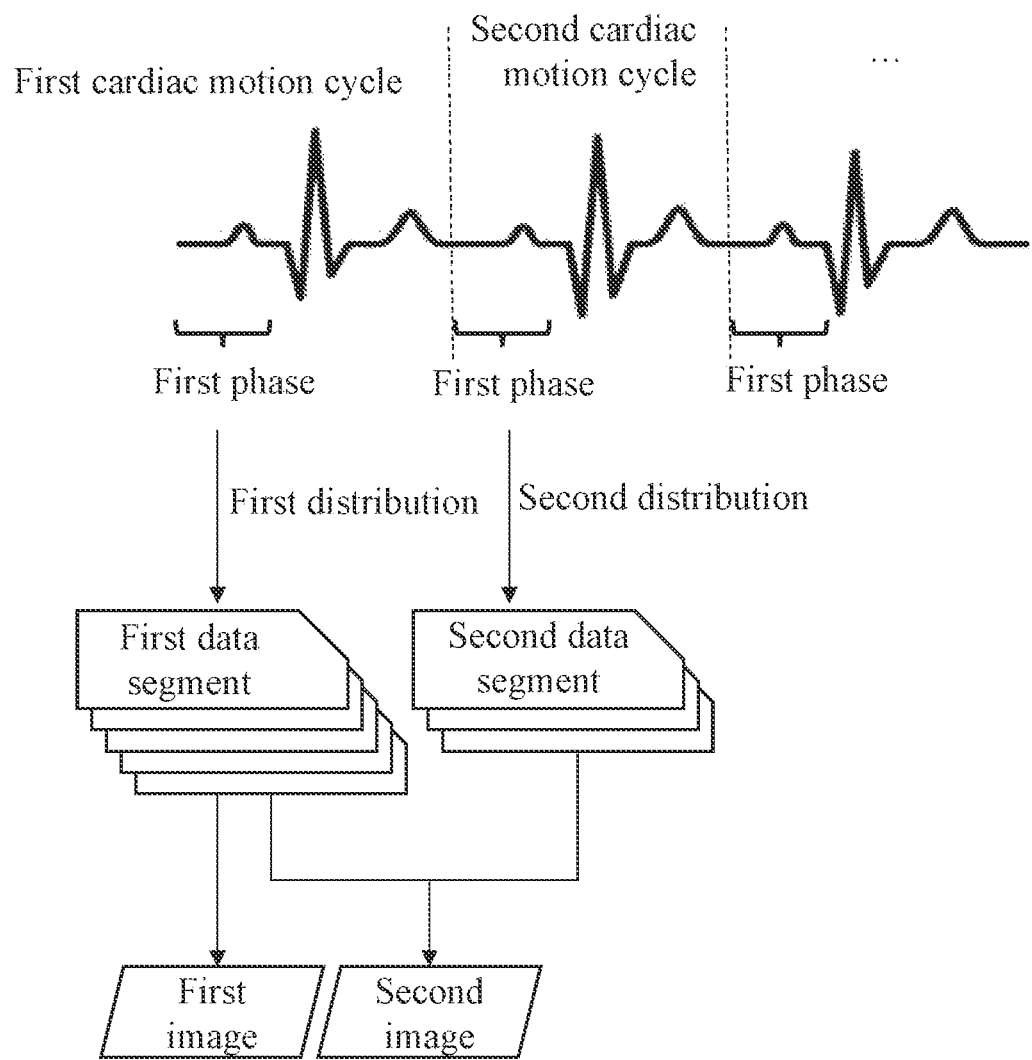
FIG. 4 is a schematic diagram of first imaging data according to some embodiments of the present disclosure.

FIG. 4 is a schematic diagram of first imaging data according to some embodiments of the present disclosure.

In some embodiments, in order to improve the data acquisition efficiency, a k-space random acquisition scheme may be adopted to acquire the first imaging data. Specifically, for images of a same phase, positions of data acquired in different phases in the k-space may be random. For example, k-space data lines of each image may not be equidistantly arranged. In addition, considering that a central region of the k-space may contain more information than an edge region of the k-space, a variable probability random distribution of the k-space may be used for acquisition, wherein a data acquisition probability of the central region of the k-space may be higher than a data acquisition probability of the edge region of k-space. In this way, more data of the central region of k-space with relatively high information content may be acquired. In some embodiments, the k-space data acquisition scheme may be preset. In some embodiments, the k-space data acquisition scheme may also be generated by an algorithm at a scanning preparation.

In some embodiments, first imaging data may include a first data segment and a second data segment. A data segment may refer to a part of data, and the data segment may be obtained by dividing the data in any way.

The first data segment and the second data segment may correspond to a same phase of one or more cardiac cycles. For example, as shown in FIG. 4, the first data segment may correspond to data of a first phase in a first cardiac cycle, and the second data segment may correspond to data of the first phase in a second cardiac cycle.

In some embodiments, the first data segment may be acquired according to a first distribution, and the second data segment may be acquired according to a second distribution. The first distribution and the second distribution may refer to data distribution when data is acquired. For example, the distribution may refer to a sampling manner in the k-space. The first distribution and the second distribution may be different and form a certain degree of complementarity.

In some embodiments, at least one of the first distribution and the second distribution may satisfy an integrity requirement for reconstructing a first image. The first image may belong to an image in a first cine. The first cine may refer to a generated cardiac cine, such as a cine with relatively low imaging quality. Satisfying the integrity requirement for reconstructing the first image may refer to the distribution of the data segment may allow data of the data segment to form the first image after reconstruction and satisfy the quality requirement of the first cine.

In some embodiments, the first data segment and the second data segment may be commonly used to reconstruct a second image. The second image may belong to a second cine. The second cine may refer to a generated cardiac cine, such as a cine with relatively high imaging quality. The reconstruction module may combine the first data segment with the second data segment to generate the second image of a relatively higher quality. Other data may also be included in such a combination.

According to methods of some embodiments, in one acquisition process, acquired data may satisfy both the reconstruction requirement of the first cine and the reconstruction requirement of the second cine at the same time. The first cine may be based on fewer data and less affected by physiological motion. The second cine may be based on more data and have a relatively high image quality. Such methods may make the cardiac cine better satisfy the requirement and reduce repeated scans.

In some embodiments, an acquisition rate of a union of the first distribution and the second distribution in a central region of k-space may be higher than an acquisition rate in an edge region, thereby making the reconstructed image have a relatively high quality and reducing the amount of data acquired.

In some embodiments, the data acquisition module 210 may dynamically determine a distribution of the acquired data (i.e., the first distribution and/or the second distribution) based on real-time reference information. For example, the distribution of the acquired data in the k-space may be determined. The real-time reference information may be acquired through ECG, respiratory monitoring, etc.

In some embodiments, when the data acquisition module 210 determines current arrhythmia and/or respiratory abnormality of a patient based on the real-time reference information, a sampling rate of a current first distribution and/or a current second distribution may be reduced. In some embodiments, the data acquisition module 210 may determine the first distribution and/or the second distribution based on a preset acquisition period. As used herein, the acquisition period may be a time length of each data acquisition. For example, if the acquisition period is long, the sampling rate of the first distribution and/or the second distribution may be reduced.

In some embodiments, cardiac cines may include the first cine and the second cine. More descriptions of the first cine and the second cine may be referred to other parts of the present disclosure, but may also be acquired in a way other than the embodiment of the present disclosure.

Figure 5:
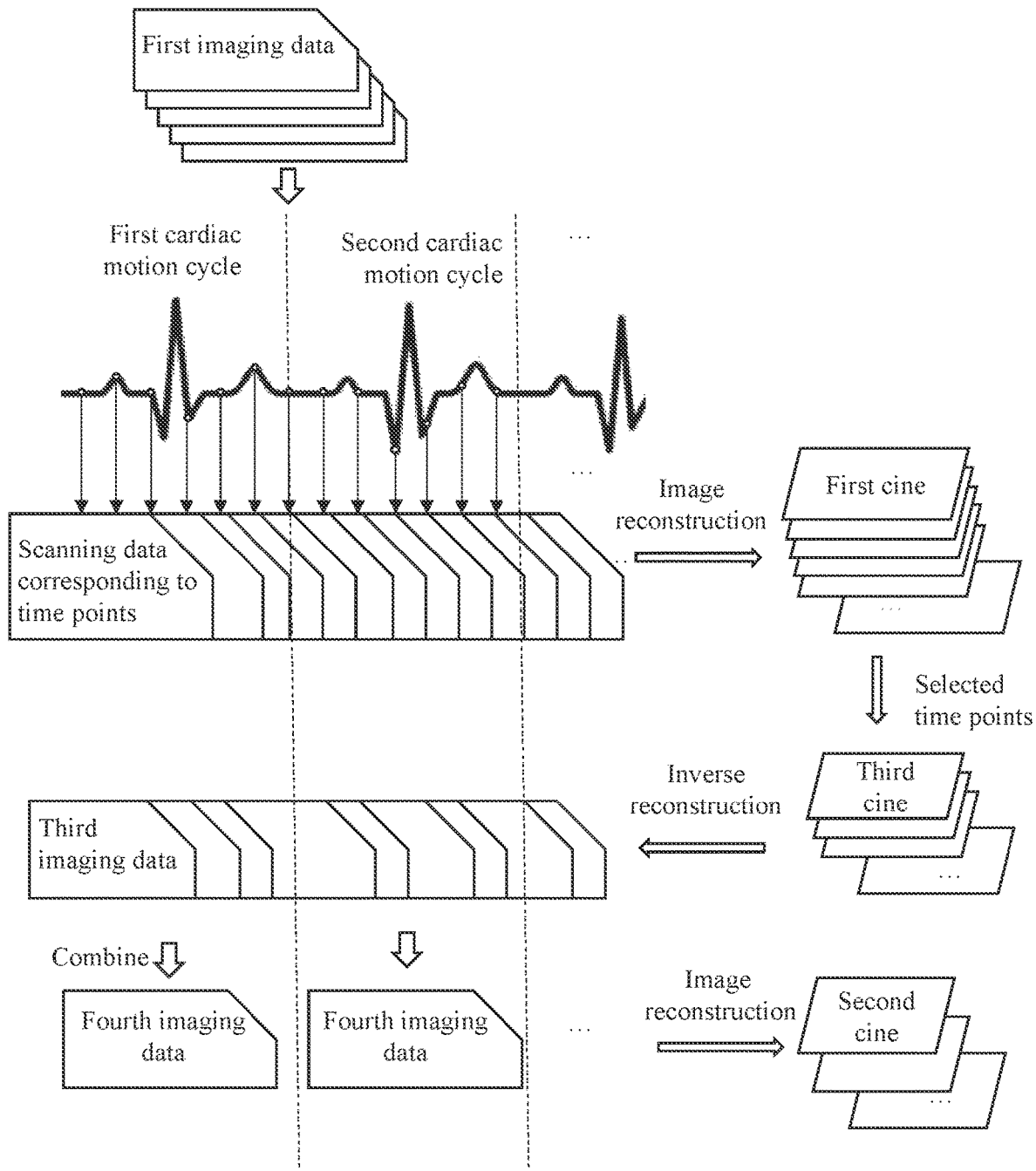
FIG. 5 is a schematic diagram of image reconstruction according to some embodiments of the present disclosure.

FIG. 5 is a schematic diagram of image reconstruction according to some embodiments of the present disclosure.

In some embodiments, the reconstruction module 220 may perform image reconstruction based on scanning data corresponding to a plurality of time points in first imaging data to acquire a first cine composed of a plurality of first image sequences.

The time point may be a time difference between a target time and a starting point of the scanning time. Of course, other reference points may be used instead of the starting point of the scanning time. A difference between a time point and a phase may be that the phase may be relative to the starting point of a cardiac cycle, and one phase may correspond to a plurality of time points of different cardiac cycles.

For example, the first cine may be a real-time dynamic cine, and there may be a fixed time interval between time points. A data acquisition manner of the real-time dynamic cine imaging may be very close to a traditional cine shot with film. The real-time dynamic cine imaging may acquire data according to a fixed time interval/frequency, which may complete an acquisition of the k-space data of a cardiac image within a fixed time interval. For example, an acquisition of the k-space data of a first cardiac image may be completed in an interval $t_0-(t_0+T)$, and an acquisition of the k-space data of the second cardiac image may be completed in an interval $(t_0+T)-(t_0+2T)$, . . . , and so on. It can be understood that "real-time" in the real-time dynamic cine imaging may refer to a real-time nature of the data acquisition, which may not necessarily mean that the image can be viewed in real-time (that is, the images may be reconstructed after acquisition).

The first imaging data may be acquired in a real-time dynamic imaging manner, and the first cine (e.g., the real-time dynamic cine) may be reconstructed based on the first imaging data. Since the first imaging data may include data corresponding to at least two cardiac cycles, a second cine (e.g., the ECG gated cardiac cine) may also be reconstructed based on the first imaging data by using the periodicity of a cardiac motion.

In some embodiments, the reconstruction module 220 may combine a portion of the first imaging data corresponding to a same phase in each cardiac motion cycle according to the reference information to acquire the fifth imaging data. Further, the reconstruction module 220 may perform the image reconstruction based on the fifth imaging data to acquire the second cine (e.g., the ECG gated cardiac cine). As used herein, the reference information may be used to locate (or obtain) phases of the at least two cardiac cycles. In some embodiments, when the reference information is a cardiac motion signal, a first extraction module 250 may extract the cardiac motion signal from the reconstructed dynamic cine.

In some embodiments, the reconstruction module 220 may perform conversion processing based on the first cine to acquire third imaging data and reconstruct the second cine image (e.g., an ECG gated cardiac cine) by combining the third imaging data.

The third imaging data may refer to data acquired by the conversion process. For example, the third imaging data may include k-space data. In some embodiments, the conversion process may include inverse reconstruction of the k-space data based on a third image. The inverse reconstruction may be a process of acquiring scanning data based on an image. The inverse reconstruction may be performed based on common manners (such as a projection algorithm, a Fourier transform, etc.).

The third image may be an image at a selected time point in the first cine, for example, all time points, a partial cardiac cycle, a time corresponding to a partial phase, or a time point determined in combination with the reference information, etc.

In some embodiments, the reconstruction module 220 may multiply pixel points in the third image by a corresponding coil sensitivity function in a scanning matrix of the imaging device, and then perform Fourier transform on the multiplied result to acquire corresponding k-space data, that is, the third imaging data.

In some embodiments, the reconstruction module 220 may combine the third imaging data according to the reference information to acquire fourth imaging data. Further, image reconstruction may be performed based on the fourth imaging data to acquire the second cine. In such a method, the first cine used herein may often include data of a plurality of cardiac cycles.

The reference information may be used to locate (or obtain) phases of data in at least two cardiac cycles. The combination may be performed on portions corresponding to a same phase in the plurality of cardiac cycles. The combination may be based on various ways, such as a combination of k-space data. The combination may also be adjusted based on the reference information. For example, spatial positions corresponding to data may be adjusted based on different respiratory states of two different time points.

The k-space data (i.e., the third imaging data) restored (or rebuilt) from the first cine (e.g., the real-time dynamic cine) may have more information and data than the directly acquired k-space data (i.e., the first imaging data), so it may be helpful to improve the quality/effect of the reconstructed dynamic image (i.e., the second cine, such as the ECG gated cardiac cine). In some embodiments, an inverse reconstruction may be performed on the first cine to restore the k-space data. Through the methods of some embodiments described above, the second cine may be acquired by combining data of the plurality of cardiac cycles, so that the second cine may have a relatively high quality.

For example, the second cine may include an ECG gated cardiac cine. The ECG gated cardiac cine imaging may take advantage of a periodicity of cardiac motions, and data acquisition may usually last for a plurality of cardiac motion cycles (also referred to as cardiac cycles). As used herein, the k-space data of each cardiac image may be divided into a plurality of parts, and each part of the k-space data of each cardiac image may be acquired within one cardiac cycle, and a plurality of cardiac cycles may be required to complete acquisition of the k-space data of one cardiac image. That is, the k-space data acquired in the plurality of cardiac cycles may be combined, and the cardiac cine (the ECG gated cardiac cine) may be reconstructed based on the combined k-space data. The second cine (e.g., the ECG gated cardiac cine) imaging may acquire data with a relatively low acceleration ratio to acquire dynamic images of relatively high quality, however it may require a patient to hold the breath for a long time without arrhythmia symptoms. Imaging of the first cine (e.g., the real-time dynamic cine) may not require the patient to hold the breath for a long time and may also be used for a patient with arrhythmia. However, the imaging of the first cine may acquire data at a relatively high acceleration ratio, a spatial resolution of an acquired image may usually be low, and a noise/artifact problem may be serious.

In some embodiments, during the obtaining of the third imaging data, the data corresponding to different cardiac cycles may have different distributions. The meaning of distribution may be found in other parts of the present disclosure. Thus, information of different parts may be better complemented when combined.

In some embodiments, the conversion process may also include respiratory motion compensation. As mentioned above, the imaging of the second cine (e.g., the ECG gated cardiac cine) may require the patient to hold the breath to cooperate with the scan. If the patient cannot hold the breath, the presence of respiratory motions may affect the reconstruction of the cardiac image (cine), for example, motion artifacts may appear in the cardiac image. For patients who cannot hold their breath, motion correction (or compensation) may be performed on the acquired data to minimize or even eliminate an impact of the respiratory motions on the image reconstruction.

Figure 6:
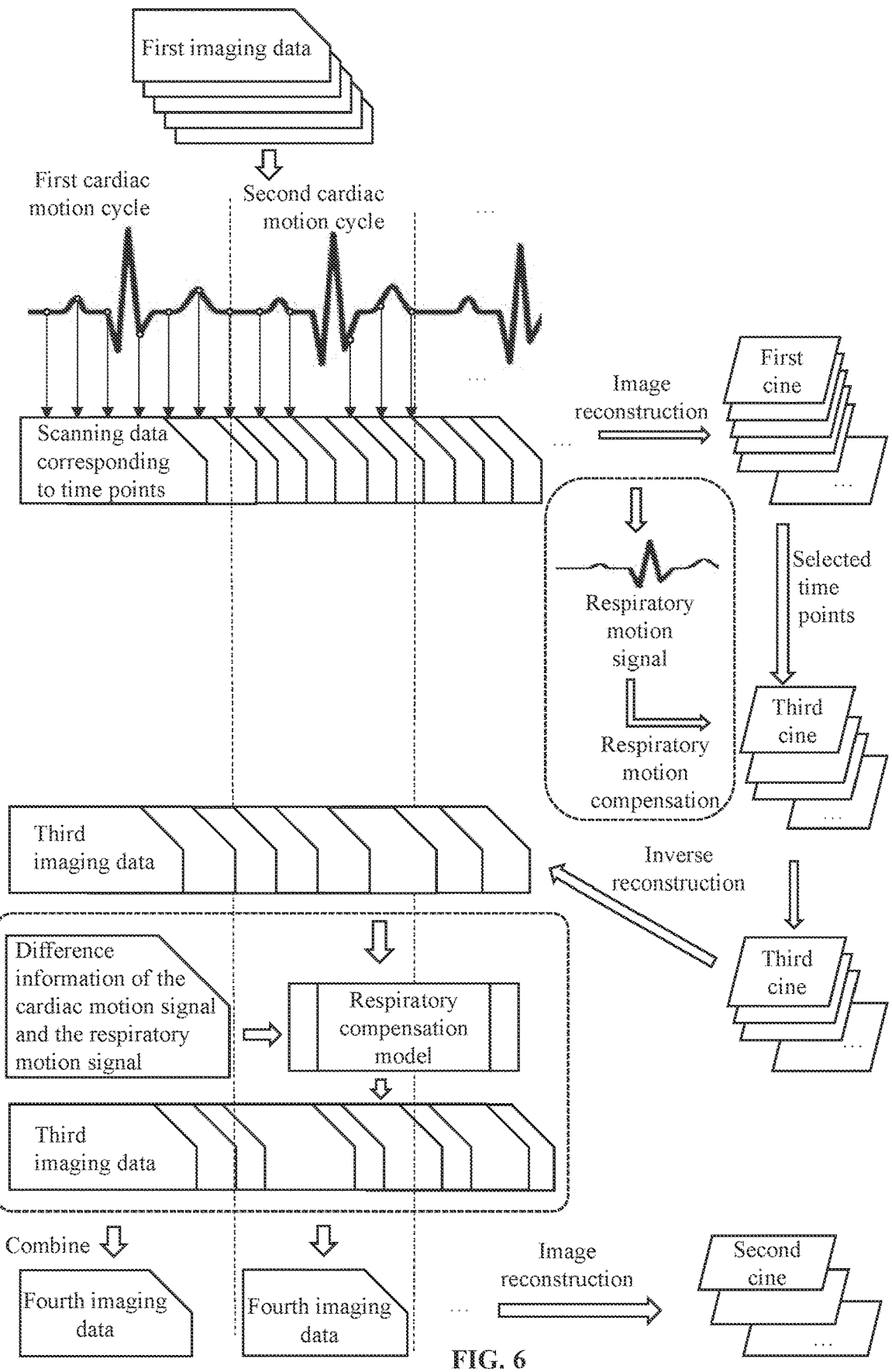
FIG. 6 is a schematic diagram of image reconstruction based on a respiratory compensation according to some embodiments of the present disclosure.

FIG. 6 is a schematic diagram of image reconstruction based on a respiratory compensation according to some embodiments of the present disclosure.

In some embodiments, the reconstruction module 220 may perform respiratory motion compensation on at least a part of a third image before inverse reconstruction. In some embodiments, the reconstruction module 220 may extract a respiratory motion signal from a first cine using various feasible manners such as image recognition before the inverse reconstruction.

Further, in some embodiments, the reconstruction module 220 may perform the respiratory motion compensation on the at least a part of the third image according to the respiratory motion signal, that is, adjust the third image according to different breathing. The compensation may be performed by various algorithms, such as a machine learning model.

For example, the data acquisition module 210 may extract the cardiac motion signal and the respiratory motion signal from the real-time dynamic cine. The reconstruction module 220 may perform respiratory motion compensation on the reconstructed real-time dynamic cine according to the cardiac motion signal and the respiratory motion signal to acquire the compensated real-time dynamic cine. Accordingly, the reconstruction module 220 may restore (or rebuild) the compensated real-time dynamic cine to the k-space to acquire the third imaging data. Then, the reconstruction module 220 may combine a portion of the third imaging data corresponding to a same phase in each cardiac motion cycle according to the cardiac motion signal to acquire the fourth imaging data. Further, the reconstruction module 220 may perform the image reconstruction based on the fourth imaging data to acquire the ECG gated cardiac cine. Through the respiratory compensation, an influence of respiration during the scanning process may be reduced, and the quality of cardiac cines may be improved.

In some embodiments, the reconstruction module 220 may select data corresponding to a plurality of time points corresponding to a phase from the first imaging data for the image reconstruction to acquire a first image frame. In some embodiments, the reconstruction module 220 may select data corresponding to at least one time point from the first imaging data based on the reference information. For example, based on the respiratory motion signal, at least one time point with a same phase and a similar respiratory state may be selected from the first imaging data, and a frame of a cardiac image may be acquired based on corresponding data reconstruction of the at least one time point. As another example, based on ECG, first sub imaging data corresponding to one or more same time points in a cardiac cycle may be selected from the first imaging data.

In some embodiments, the reconstruction module 220 may select a plurality of time points corresponding to a same phase from a plurality of cardiac cycles, and acquire a plurality of first sub imaging data based on the plurality of time points. In some embodiments, when the reconstruction module 220 performs reconstruction based on data from different cardiac cycles, the reconstruction module 220 may reconstruct the data separately and fuse reconstructed images. In some embodiments, a fusion manner may include, but be not limited to averaging weighted averaging, or the like, or any combination thereof. In some embodiments, parameters of the fusion, such as a weight of a weighted average, may be related to the reference information. For example, data acquired at a time period when the heart motion is relatively normal may have a relatively high weight.

In some embodiments, the reconstruction module 220 may reconstruct the cardiac image quickly after the acquisition of the scanning data. "Quickly" used herein may refer that a reconstructed image is sufficient for subsequent processing, such as affecting a period of subsequent acquisition, a scan distribution, etc. In some embodiments, a portion of the scanning data may be extracted for the quick reconstruction, for example, based on a lower sampling rate. For example, the reconstruction may be completed before a start of a corresponding phase of a next cardiac cycle. An image of the quick reconstruction may not satisfy some viewing requirements (such as diagnosis) as long as the image of the quick reconstruction satisfies the requirement of extracting specific information. For example, the specific information may be cardiac information, respiratory information, etc.

In some embodiments, after the inverse reconstruction, the reconstruction module 220 may perform the respiratory motion compensation on third imaging data in a frequency domain to remove an influence of respiration on the data.

In some embodiments, the reconstruction module 220 may input the third imaging data, difference information of the cardiac motion signal, and/or difference information of the respiratory motion signal into a respiratory compensation model, and output compensated third imaging data. The respiratory compensation model may include a machine learning model, such as a deep neural networks (DNN) model. The respiratory compensation model may be acquired by training based on a gold standard, which may be acquired by high-quality scanning or other manners.

For a patient with the arrhythmia, a reconstruction of the second cine (e.g., the ECG gated cardiac cine) may also be affected since the second cine (e.g., the ECG gated cardiac cine) may mainly use the periodicity of the cardiac motion to reconstruct the image. In order to minimize an influence of the arrhythmia on the second cine (e.g., the ECG gated cardiac cine) reconstruction, the reconstruction module 220 may combine only data from cardiac cycles within a preset time interval during combination processing on the k-space data (such as the first imaging data and the third imaging data), without using (or eliminating) the data (corresponding to arrhythmia data) from cardiac cycles outside the preset time interval. For example, an error of a cardiac cycle may be limited to no more than 50 ms based on 800 ms, that is, the time interval may be 750 ms to 850 ms. In practical applications, the time interval may be set by a user (such as a doctor).

In some embodiments, the reconstruction module 220 may perform the reconstruction by combining the reference information and a reference image. The reference image may be an image selected for reconstruction.

During the reconstruction, the selected reference image may be adjusted and reconstructed again based on an evaluating result of previously reconstructed cardiac cines. The reference image may also be selected in combination with the reference information. For example, data of a plurality of periods in which the reference information and the reference image are relatively consistent may be selected to be combined as data of a common reconstructed image.

In some embodiments, images may be reconstructed based on a plurality of different groups of data corresponding to a same phase, respectively. The data to be used may be selected based on the quality of a reconstructed image. The quality may be evaluated based on the reconstructed image or predicted by a machine learning model. Such method may be combined with other embodiments. For example, when there are a plurality of data segments with a second distribution, an appropriate data segment may be selected by the above method for reconstruction in combination with one or more data segments with a first distribution.

In some embodiments, the reconstruction module 220 may use an image quality prediction model and/or an image quality evaluation model to determine whether each frame of a second cardiac image satisfies the quality requirement based on a preset threshold (or score). For example, if an output score of the image quality prediction model and/or the image quality evaluation model based on an input second image is greater than the preset threshold (or score), the second image may be determined to satisfy the quality requirement, otherwise, the second images may be determined to not satisfy the quality requirement. In some embodiments, the reconstruction module 220 may designate the second image that satisfies the quality requirement as an image in the second cine.

In some embodiments, the reconstructed second cine (e.g., an ECG gated cardiac cine) and/or the first cine (e.g., a real-time dynamic cine) may be automatically evaluated by a machine, such as the processing device 130. An evaluation basis (i.e., input) may include one or more of the following information: the acquired k-space data, the acquired other reference information (such as ECG, pulse signals, cardiac motion signals, respiratory motion signals, etc.), and/or the reconstructed cardiac cine. Accordingly, a result (output) of the evaluation may include a degree (e.g., existence or non-existence, slight/moderate/severe, etc.) of occurrence of a target physiological phenomena (e.g., the arrhythmia, respiratory motion, etc.) during the data acquisition and/or an image quality of the cardiac cine (e.g., a score reflecting the image quality, whether the cardiac cine satisfies a diagnostic criteria, etc.).

In some embodiments, the reconstruction module 220 may evaluate the quality based on an evaluation rule. A quality evaluation parameter involved in the evaluation rule may include, but be not limited to, a spatial resolution, a signal-to-noise ratio, a contrast, etc. The quality evaluation parameter may be acquired in various manners, such as a manner based on histogram statistics.

In some embodiments, the reconstruction module 220 may acquire at least one of the cardiac motion signal and the respiratory motion signal for quality evaluation. For example, in a preset rule, scores of different cardiac cines may be adjusted differently according to the stability of the cardiac motion. As another example, in a case of a large respiratory fluctuation, a quality score may be relatively low. By introducing these signals, the quality evaluation may be made more accurate.

In some embodiments, the processing device may use one or more parameters of the imaging device for the quality evaluation. The one or more parameters may include, but be not limited to, a scanning matrix of the imaging device, a count of excitation of a pulse sequence, a repetition time, an echo time, or the like.

In some embodiments, the automatic evaluation mentioned in the present disclosure may be realized by an artificial intelligence technique. For example, a large amount of labeled sample data may be used to train a machine learning model, and the trained machine learning model may be used for the evaluation. Referring to the foregoing descriptions, the label here may refer to labeling the image quality and the degree of the target physiological phenomena (such as the arrhythmia and the respiratory movement) during the data acquisition.

In some embodiments, the processing device may perform the quality evaluation on the generated cardiac cine through a first model. An input of the first model may include one or more of scanning information, reference information, or a reconstruction parameter. A feature of the input may include contents of some embodiments in other parts of the present disclosure, and may also include other information.

The first model may be a machine learning model, such as a neural network model. The first model may be acquired by training data and label training. Labels may be acquired based on manual calibration or by other manners.

The first model does not use images for evaluation, which may have high efficiency and may also predict the quality before the generation of the cardiac cine. In some cases, the result based on the first model may be used to quickly determine a strategy of data scanning, data acquiring, or data processing, including but being not limited to an acquisition period, a sampling rate, a distribution, a manner of generating the cardiac cine, etc.

In some embodiments, the processing device may perform the quality evaluation on the generated cardiac cine through a second model. An input of the second model may include part or all of images of the generated cardiac cine, and may also include other information, such as information involved in the description of the first model or others. The other information may need not be limited by the input of the first model.

In some embodiments, an output of the second model may include a quality score or a continuity score.

In some embodiments, a structure within the second model may include: respectively inputting a plurality of images into a feature extraction layer (e.g., composed of CNN or other structures) to acquire a plurality of embedded features respectively; respectively inputting at least a portion of the plurality of embedded features into a quality scoring layer (e.g., composed of neural networks or other structures) to acquire quality scores corresponding to the images, and acquiring a quality score of a cardiac cine by summing and weighted averaging. In some embodiments, the weight may be related to other information. For example, the weight may be related to a phase of a corresponding image in a cardiac cycle. For example, a less important phase may have a lower weight; inputting at least a portion of the plurality of embedded features into a continuity scoring layer based on a sequence (e.g., Long Short-Term Memory (LSTM), Bidirectional Encoder Representation from Transformer (BERT)) to acquire the continuity scores;

In some embodiments, the embedded features entering the quality scoring layer may be less than the embedded features entering the continuity scoring layer, thereby reducing a complexity of the model.

In some embodiments, the input of the quality scoring layer may include other information input by the second model, such as one or more parameters of the scanning device, etc.

In some embodiments, the input of the continuity scoring layer may include other information of the second model input, such as a stability of breathing, etc.

The structure of the second model may also include various changes, including adding other processing, executing only a part as described above, etc. The second model of the above structure may be acquired through joint training.

The training data and the labels may be acquired in various ways. In some embodiments, quality score data and the labels may be acquired based on data of different sampling rates and different stabilities. For example, image samples reconstructed from data with a low sampling rate and a poor stability may be labeled with low quality scores. For example, the image samples reconstructed from data with high noise, high artifact, and low spatial resolution may be labeled with low quality scores.

In some embodiments, the data and the labels used for training the stability scores may be acquired by splicing data at different time periods. For example, a cine sample may be acquired by exchanging data of a same phase in different cycles, and giving a label with a low continuity score.

Referring to the foregoing descriptions, in addition to overcoming the adverse effect of the target physiological phenomena on the image reconstruction by some measures (such as limiting a length of cardiac cycle and the respiratory motion compensation), a degree of the target physiological phenomena occurring during the data acquisition may also be evaluated. The evaluation result may be used to further evaluate the image quality of the cardiac cine (especially the ECG gated cardiac cine). For example, the evaluation result of the degree of the target physiological phenomena occurring during the data acquisition may be used as a basis for evaluating the image quality.

In some embodiments, the processing device 130 may determine output dynamic cine information based on one or more quality evaluation results of one or more cardiac cines.

The cardiac cine information may include various types of information related to the one or more cardiac cines. The cardiac cine information may include the one or more cardiac cines or related parameter information thereof. For example, the parameter information may include a generation manner, quality information, or the like. The output may be implemented in various manners. For example, a cardiac cine of a relatively high quality may be selected to output. As another example, quality evaluation parameters of different cardiac cines may be output for user selection, etc.

After obtaining an automatic evaluation result, only cardiac cines with better image quality indicated by the evaluation result may be output to the user, or two types of cardiac cines (real-time dynamic cines and ECG gated cardiac cines) and the evaluation result may be output to the user, so that the user may select one type of cardiac cines for diagnosis by referring to the evaluation result. In some embodiments, when two types of cardiac cines are output to the user, cardiac cines with a better image quality indicated by the evaluation result may be recommended to the user at the same time.

In some embodiments, the image reconstruction of a first cardiac cine may be performed first, and the image quality of the first cardiac cine may be evaluated, and then whether to continue the image reconstruction of a cardiac cine of a second type may be determined according to the evaluation result. The first type may refer to one type of the first cine and the second cine, and the second type may refer to the other type of the first cine and the second cine. When the evaluation result indicates that the image quality of the cardiac cine of the first type satisfies diagnostic criteria, the image reconstruction of the cardiac cine of the second type may not be performed. Otherwise, the image reconstruction of the cardiac cine of the second type may be continued. Thus, a diagnostic efficiency may be improved. It should be noted that in some embodiments, the reconstruction of the second cine may depend on the reconstruction of the first cine. In this case, the first type may specifically refer to the first cine. In addition, the evaluation of the image quality of the cardiac cine of the first type may be an automatic evaluation of a machine or a manual evaluation (for example, the user evaluates and inputs the evaluation result).

According to the embodiments provided in the present disclosure, two types of the cardiac cines may be reconstructed based on one scan, that is, the first cine (the real-time dynamic cine) and the second cine (the ECG gated cardiac cine). After outputting the two types of cardiac cines, a user (such as a doctor) may choose a cardiac cine that satisfies his/her need. During a traditional diagnosis process, the reconstructed cardiac cine may be not ideal and need to be scanned again in a replacement manner. A scanning time may be reduced and a diagnosis efficiency may be improved compared to the traditional diagnosis process.

In some embodiments, one type of the cardiac cines may be output first, and then determine whether to output another type of the cardiac cines according to a user instruction. Since there may be a possibility that the cardiac cine outputs first may satisfy the need of diagnosis, by selectively outputting another type of the cardiac cines, a time for a user (such as a doctor) to view the cardiac cines may be saved as a whole, thereby improving the diagnosis efficiency.

For example, the second cine (e.g., an ECG gated cardiac cine) may be output first, and then whether to output the first cine (e.g., a real-time dynamic cine) may be determined according to the user instructions. As another example, the output module 230 may output the first cine first, and then determine whether to output the second cine according to a user instruction. Specifically, after the output of one type of the cardiac cines, the processing device 130 or the terminal device 150 connected to the processing device 130 may request the user to indicate whether to output another type of the cardiac cines, for example, by asking the user whether to output another type of cardiac cine through a pop-up dialog box. If the user thinks that the currently outputted cardiac cine satisfies the requirement, the user may select a "no" button, accordingly, the output module 230 may no longer output the another type of the cardiac cines. If the user thinks that the currently outputted cardiac cine does not satisfy the requirement, the user may select a "yes" button, and accordingly, the output module 230 may continue to output the another type of the cardiac cines.

In some embodiments, a user (such as a doctor) may select which type of the cardiac cines (the first cine or the second cine) to output first. That is, the output module 230 may also determine a type of the cardiac cines to be output first according to the user instruction. In a practical application, the user may select the type of cardiac cine to be outputted first according to experience, preference, etc. For example, in the process 400, the user may find that the acquired second cine may be more effective than the first cine (for example, 6 or more times out of 10 times). Therefore, the user may select to output the second cine first.

In some embodiments, the cardiac cine may need to be output in a compressed form. In this case, an evaluation method for the compressed image may be adopted, and the evaluation method may be used to select an appropriate image (or video) compression technology. For example, if losses caused by different compression technologies to the image quality of the cardiac cine are able to be evaluated, the compression technology that causes the least loss to the image quality of the cardiac cine may be selected.

In some embodiments, one or more of the mean square error (MSE), a peak signal to noise rate (PSNR), a structural similarity (SSIM), and other techniques may be used to perform an image quality evaluation.

After obtaining the automatic evaluation result, only the cardiac cine with better image quality indicated by the evaluation result may be output to the user, or two types of the cardiac cines (the real-time dynamic cine and the ECG gated cardiac cine) and the evaluation result may be output to the user, so that the user may select one type of the cardiac cines for diagnosis by referring to the evaluation result. In some embodiments, when two types of the cardiac cines are output to the user, a cardiac cine with better image quality indicated by the evaluation result may be recommended to the user at a same time.

In some embodiments, the image reconstruction of a first type of the cardiac cine may be performed first, and the image quality of the first type of cardiac cine may be evaluated, and then whether to continue the image reconstruction of a second type of cardiac cine may be determined according to the evaluation results. As used herein, the first type may refer to one type of the real-time dynamic cine and the ECG gated cardiac cine, and the second type may refer to the other type of the real-time dynamic cine and the ECG gated cardiac cine. If the evaluation result indicates that the image quality of the first type of the cardiac cines satisfy the diagnostic criteria, the image reconstruction of the second type of the cardiac cines may not be performed. Otherwise, the image reconstruction of the second type of the cardiac cine may be continued. Thus, the diagnostic efficiency may be improved. It should be noted that in some embodiments, the reconstruction of the ECG gated cardiac cine may depend on the preceding reconstruction of the real-time dynamic cine. In this case, the first type may specifically refer to the real-time dynamic cine. In addition, the evaluation of the image quality of the first type of cardiac cine may be an automatic evaluation of a machine or a manual evaluation (for example, the user may evaluate and input the evaluation result).

The basic concepts have been described above. Obviously, for those skilled in the art, the above-detailed disclosure is only an example and does not constitute a limitation of the present disclosure. Although it is not explicitly stated here, those skilled in the art may make various modifications, improvements and amendments to the present disclosure. Such modifications, improvements and amendments are suggested in the present disclosure, so such modifications, improvements and amendments still belong to the spirit and scope of the exemplary embodiments of the present disclosure.

Meanwhile, the present disclosure uses specific words to describe the embodiments of the present disclosure. For example, "one embodiment", and/or "some embodiments" mean a certain feature or structure related to at least one embodiment of the present disclosure. Therefore, it should be emphasized and noted that "one embodiment" or "an alternative embodiment" mentioned twice or more in different positions in the present disclosure does not necessarily refer to the same embodiment. In addition, certain features or structures in one or more embodiments of the present disclosure may be appropriately combined.

In addition, unless explicitly stated in the claims, the sequence of processing elements and sequences, the use of numbers and letters, or the use of other names described in the present disclosure are not used to define the sequence of processes and methods in the present disclosure. Although the above disclosure has discussed some currently considered useful embodiments of the invention through various examples, it should be understood that such details are only for the purpose of explanation, and the additional claims are not limited to the disclosed embodiments. On the contrary, the claims are intended to cover all amendments and equivalent combinations that conform to the essence and scope of the embodiments of the present disclosure. For example, although the system components described above can be implemented by hardware devices, they can also be implemented only by software solutions, such as installing the described system on an existing server or mobile device.

Similarly, it should be noted that, in order to simplify the description disclosed in the present disclosure and thus help the understanding of one or more embodiments of the invention, the foregoing description of the embodiments of the present disclosure sometimes incorporates a variety of features into one embodiment, the drawings or the description thereof. However, this disclosure method does not mean that the object of the present disclosure requires more features than those mentioned in the claims. In fact, the features of the embodiments are less than all the features of the single embodiments disclosed above.

In some embodiments, numbers describing the number of components and attributes are used. It should be understood that such numbers used in the description of embodiments are modified by the modifiers "about", "approximate" or "substantially" in some examples. Unless otherwise stated, "approximately" or "substantially" indicate that the figure allows a variation of ±20%. Accordingly, in some embodiments, the numerical parameters used in the description and claims are approximate values, which may be changed according to the characteristics required by individual embodiments. In some embodiments, the numerical parameters should take into account the specified significant digits and adopt the general bit retention method. Although in some embodiments of the present disclosure, the numerical range and parameters used to confirm the range are approximate values, in specific embodiments, the setting of such values is as accurate as possible within the feasible range.

For each patent, patent application, patent application publication and other materials cited in the present disclosure, such as articles, books, specifications, publications, documents, etc., the entire contents are hereby incorporated into the present disclosure for reference. The application history documents that are inconsistent with or conflict with the contents of the present disclosure are excluded, and the documents that limit the broadest scope of claims in the present disclosure (currently or later attached to the present disclosure) are also excluded. It should be noted that if there is any inconsistency or conflict between the description, definition, and/or use of terms in the supplementary materials of the present disclosure and the contents described in the present disclosure, the description, definition, and/or use of terms in the present disclosure shall prevail Finally, it should be understood that the embodiments described in the present disclosure are only used to illustrate the principles of the embodiments of the present disclosure. Other deformations may also fall within the scope of the present disclosure. Therefore, as an example rather than a limitation, the alternative configuration of the embodiments of the present disclosure can be regarded as consistent with the teachings of the present disclosure. Accordingly, the embodiments of the present disclosure are not limited to those explicitly introduced and described in the present disclosure.

What is claimed is:

1. An imaging method, comprising:
obtaining first imaging data acquired by an imaging device, wherein the first imaging data includes data corresponding to a plurality of cardiac cycles;
performing image reconstruction on data corresponding to a plurality of time points in the first imaging data to acquire a first cine, wherein the first cine includes cardiac images corresponding to the plurality of time points, and there is a fixed time interval between adjacent time points among the plurality of time points;
generating a second cine that includes cardiac images of a plurality of phases in at least one cardiac cycle based on the first cine and reference information, wherein the reference information is used to locate one or more phases of the plurality of cardiac cycles.

2. The method of claim 1, wherein
the first imaging data includes a first data segment and a second data segment, wherein the first data segment and the second data segment correspond to a same phase of one or more cardiac cycles;
the first data segment is acquired according to a first distribution, the second data segment is acquired according to a second distribution, the first distribution and the second distribution being different sampling manners in k-space;
at least one of the first distribution and the second distribution satisfies an integrity requirement for reconstructing a first image, the first image belonging to the first cine; and
the first data segment and the second data segment are used to reconstruct a second image, the second image belonging to the second cine.

3. The method of claim 2, wherein an acquisition rate of a union of the first distribution and the second distribution in a central region of k-space is higher than an acquisition rate in an edge region.

4. The method of claim 1, further comprising:
acquiring the reference information, the reference information including a cardiac motion signal; and
determining the plurality of phases from the first imaging data based on the reference information.

5. The method of claim 1, wherein the reference information includes a cardiac motion signal determined based on the first cine.

6. The method of claim 1, further comprising:
acquiring the first imaging data by performing abnormal processing on second imaging data acquired from the imaging device.

7. The method of claim 6, wherein the abnormal processing includes removing abnormal data, the abnormal data including data corresponding to abnormal heart rhythms or abnormal breathing.

8. The method of claim 1, wherein the generating a second cine comprises:
performing conversion processing based on the first cine to acquire third imaging data, the third imaging data including k-space data, the conversion processing including an inverse reconstruction of k-space data based on a third image, the third image being an image in the first cine acquired at a selected time point;
combining a plurality of parts of the third imaging data corresponding to a same phase in the plurality of cardiac cycles according to the reference information to acquire fourth imaging data; and
performing image reconstruction on the fourth imaging data to obtain the second cine.

9. The method of claim 8, wherein the conversion processing further includes:
extracting a respiratory motion signal from the first cine before the inverse reconstruction;
performing respiratory motion compensation on at least a part of the third image according to a cardiac motion signal and the respiratory motion signal.

10. The method of claim 1, further comprising:
determining at least one of the first cine or the second cine for output to a user based on one or more quality evaluation results of the first cine and the second cine.

11. The method of claim 1, further comprising:
acquiring at least one of a cardiac motion signal or a respiratory motion signal for quality evaluation.

12. The method of claim 1, wherein the first cine is a real-time dynamic cine, and the second cine is an ECG gated cardiac cine.

13. The method of claim 12, wherein the first imaging data is acquired using an imaging manner corresponding to the real-time dynamic cine.

14. An imaging system comprising:
at least one storage device including a set of instructions;
at least one processor in communication with the at least one storage device, wherein when executing the set of instructions, the at least one processor is configured to cause the system to perform operations including:
obtain first imaging data acquired by an imaging device, wherein the first imaging data includes data corresponding to a plurality of cardiac cycles; and
perform image reconstruction based on data corresponding to a plurality of time points in the first imaging data to acquire a first cine, wherein the first cine includes cardiac images corresponding to the plurality of time points, and there is a fixed time interval between adjacent time points among the plurality of time points;
generate a second cine that includes cardiac images of a plurality of phases in at least one cardiac cycle based on the first cine and reference information, wherein the reference information is used to locate one or more phases of the plurality of cardiac cycles.

15. The system of claim 14, wherein
the first imaging data includes a first data segment and a second data segment, wherein the first data segment and the second data segment correspond to a same phase of one or more cardiac cycles;
the first data segment is acquired according to a first distribution, the second data segment is acquired according to a second distribution, the first distribution and the second distribution being different sampling manners in k-space;
at least one of the first distribution and the second distribution satisfies an integrity requirement for reconstructing a first image, the first image belonging to the first cine; and
the first data segment and the second data segment are used to reconstruct a second image, the second image belonging to the second cine.

16. The system of claim 15, wherein an acquisition rate of a union of the first distribution and the second distribution in a central region of k-space is higher than an acquisition rate in an edge region.

17. The system of claim 14, further comprising:
acquiring the reference information, the reference information including a cardiac motion signal; and
determining the plurality of phases from the first imaging data based on the reference information.

18. The system of claim 14, wherein the generating a second cine comprises:
performing conversion processing based on the first cine to acquire third imaging data, the third imaging data including k-space data, the conversion processing including an inverse reconstruction of k-space data based on a third image, the third image being an image in the first cine acquired at a selected time point;
combining a plurality of parts of the third imaging data corresponding to a same phase in the plurality of cardiac cycles according to the reference information to acquire fourth imaging data; and
performing image reconstruction on the fourth imaging data to obtain the second cine.

19. The system of claim 18, wherein the conversion processing further includes:
extracting a respiratory motion signal from the first cine before the inverse reconstruction;
performing respiratory motion compensation on at least a part of the third image according to a cardiac motion signal and the respiratory motion signal.

20. A non-transitory computer readable medium storing instructions, the instructions, when executed by at least one processor, causing the at least one processor to implement a method comprising:
obtaining first imaging data acquired by a magnetic resonance device, wherein the first imaging data includes data corresponding to a plurality of cardiac cycles;
performing image reconstruction on data corresponding to a plurality of time points in the first imaging data to acquire a first cine, wherein the first cine includes cardiac images correspond to the plurality of time points, and there is a fixed time interval between adjacent time points among the plurality of time points;
generating a second cine that includes cardiac images of a plurality of phases in at least one cardiac cycle based on the first cine and reference information, wherein the reference information is used to locate one or more phases of the plurality of cardiac cycles.

* * * * *